US007759100B2

(12) United States Patent
Hsieh

(10) Patent No.: US 7,759,100 B2
(45) Date of Patent: Jul. 20, 2010

(54) **CARBOXIN RESISTANCE GENE FOR *FLAMMULINA VELUTIPES***

(75) Inventor: Hsiu-Hsin Hsieh, Taipei (TW)

(73) Assignee: Mycomagic Biotechnology Co., Ltd., Taipei County (TW)

( * ) Notice: Subject to any disclaimer, the term of this patent is extended or adjusted under 35 U.S.C. 154(b) by 0 days.

(21) Appl. No.: 12/326,497

(22) Filed: Dec. 2, 2008

(65) Prior Publication Data

US 2010/0136664 A1 Jun. 3, 2010

(51) Int. Cl.
C12N 9/00 (2006.01)
C12Q 1/00 (2006.01)
C12Q 1/68 (2006.01)
C12N 1/20 (2006.01)
C12N 15/00 (2006.01)
C12P 21/04 (2006.01)
C07H 21/04 (2006.01)

(52) U.S. Cl. ............................ 435/183; 435/4; 435/6; 435/69.1; 435/71.1; 435/252.3; 435/320.1; 536/23.2

(58) Field of Classification Search ........................ None
See application file for complete search history.

(56) References Cited

U.S. PATENT DOCUMENTS 4,608,775 A 9/1986 Elliott et al.

OTHER PUBLICATIONS

Branden et al. Introduction to Protein Structure, Garland Publishing Inc., New York, p. 247, 1991.*
Broomfield et al. A single amino acid change in the iron-sulphur protein subunit of succinate dehydrogenase confers resistance to carboxin in Ustilago maydis. Curr. Genet. 22, 117-121, 1992.*
Toshikazu Irie et al., Cloning and Characterization of the Gene Encoding the Iron-Sulfur Protein of Succinate Dehydrogenase from *Pleurotus ostreatus*, Journal, 1998, pp. 27-31, Biochimica et Biophysics Acta 1396, Elsevier.
Y. Honda et al, Carboxin Resistance Transformation of the Homobasidiomycete Fungus *Pleurotus Ostreatus*, Journal, 2000, pp. 209-212, Curr Genet 37, Springer-Verlag.
Christopher N. Topp, et al., Integration of the Gene for Carboxin Resistance Does Not Impact the Ustilago Maydis-Maize Interaction, Journal, 2002, pp. 67-70, Current Microbiology vol. 44, Springer-Verlag New York, Inc.

* cited by examiner

*Primary Examiner*—Yong D Pak
(74) *Attorney, Agent, or Firm*—WPAT, P.C.; Anthony King

(57) ABSTRACT

The present invention pertains to a polynucleotide sequence expressed in *Flammulina velutipes* against carboxin and the proteins encoded thereby. Also provided is the expression vector and host cell comprising the polynucleotides of the invention.

4 Claims, 5 Drawing Sheets

SEQUENCE LISTING

<160> NUMBER OF SEQ ID NOS: 13

<210> SEQ ID NO 1
<211> LENGTH: 961
<212> TYPE: DNA
<213> ORGANISM: Flammulina velutipes

<400> SEQUENCE: 1

```
atgcagtccg tcgcccgtcg tttctctgcc gccgccgtgc gccgtagctt ttctaccact      60
tctgtcgcgt tccaggctac accgctcgag aagcccgtgc tgaacaagga attcaagatt     120
taccgctgga atcctgatga gccggagaag aaaccgacgc tacagagcta cataatcgac     180
ctgaaccaga cagggccaat gattctggat gctctcatca agattaaaaa cgaaatcgac     240
cctacgctta ccttcagacg aagttgtcgc gagggcattt gcggatcttg tgcgagaaaa     300
atcgacgggc agaacacgtt ggcctgtctc tgcaggattg ataggaatgc tgggaaggat     360
tcgaagatct atcccttacc acacagtgag tgtctcatct gagctctgcg tatctgagtg     420
ctaacttaga ttccagtgta catcgtcaag gacctcgtac cggatctcac ctacttctac     480
aagcagtaca agtctatcca accatacctt cagaacgaca acccacctgc gtcaggtctg     540
ttcattattt tgcaccctcc cctttgctcg gcttaccgaa tcgcttctag gtgaattcct     600
ccaaacgcaa gatgaccgca agaagctcga cggactctac gagtgtatcc tttgcgcgtg     660
ttgttcgacg tcttgccctt cgtattggtg gaaccaagac gaataccttg gacccgctac     720
tttgatgcaa gcatatcgct ggatcgccga ctcgagagta cgttctgctc gtcgtatcat     780
gttttatctc atactgatat actcttagga ctcttatgcc gcagaacgca aggaaaagct     840
ccaaaacgag atgagcatgt accgatgcct cactatcttc aactgctcgc ggacatgccc     900
caagggtctc aaccccgctg ccgccatcgc gaaaatcaag cttgagcttg cggccgagta     960
a                                                                      961
```

<210> SEQ ID NO 2
<211> LENGTH: 267
<212> TYPE: PRT
<213> ORGANISM: Flammulina velutipes

<400> SEQUENCE: 2

```
Met Gln Ser Val Ala Arg Arg Phe Ser Ala Ala Val Arg Arg Ser
1               5                   10                  15

Phe Ser Thr Thr Ser Val Ala Phe Gln Ala Thr Pro Leu Glu Lys Pro
                20                  25                  30

Val Leu Asn Lys Glu Phe Lys Ile Tyr Arg Trp Asn Pro Asp Glu Pro
            35                  40                  45

Glu Lys Lys Pro Thr Leu Gln Ser Tyr Ile Ile Asp Leu Asn Gln Thr
        50                  55                  60

Gly Pro Met Ile Leu Asp Ala Leu Ile Lys Ile Lys Asn Glu Ile Asp
65                  70                  75                  80

Pro Thr Leu Thr Phe Arg Arg Ser Cys Arg Glu Gly Ile Cys Gly Ser
                85                  90                  95

Cys Ala Arg Lys Ile Asp Gly Gln Asn Thr Leu Ala Cys Leu Cys Arg
            100                 105                 110

Ile Asp Arg Asn Ala Gly Lys Asp Ser Lys Ile Tyr Pro Leu Pro His
        115                 120                 125

Met Tyr Ile Val Lys Asp Leu Val Pro Asp Leu Thr Tyr Phe Tyr Lys
    130                 135                 140

Gln Tyr Lys Ser Ile Gln Pro Tyr Leu Gln Asn Asp Asn Pro Pro Ala
145                 150                 155                 160

Ser Gly Glu Phe Leu Gln Thr Gln Asp Asp Arg Lys Lys Leu Asp Gly
                165                 170                 175

Leu Tyr Glu Cys Ile Leu Cys Ala Cys Cys Ser Thr Ser Cys Pro Ser
            180                 185                 190

Tyr Trp Trp Asn Gln Asp Glu Tyr Leu Gly Pro Ala Thr Leu Met Gln
        195                 200                 205

Ala Tyr Arg Trp Ile Ala Asp Ser Arg Asp Ser Tyr Ala Ala Glu Arg
    210                 215                 220

Lys Glu Lys Leu Gln Asn Glu Met Ser Met Tyr Arg Cys Leu Thr Ile
225                 230                 235                 240

Phe Asn Cys Ser Arg Thr Cys Pro Lys Gly Leu Asn Pro Ala Ala Ala
                245                 250                 255

Ile Ala Lys Ile Lys Leu Glu Leu Ala Ala Glu
            260                 265
```

<210> SEQ ID NO 3
<211> LENGTH: 961
<212> TYPE: DNA
<213> ORGANISM: Flammulina velutipes

<400> SEQUENCE: 3

```
atgcagtccg tcgcccgtcg tttctctgcc gccgccgtgc gccgtagctt ttctaccact      60
tctgtcgcgt tccaggctac accgctcgag aagcccgtgc tgaacaagga attcaagatt     120
taccgctgga atcctgatga gccggagaag aaaccgacgc tacagagcta cataatcgac     180
ctgaaccaga cagggccaat gattctggat gctctcatca agattaaaaa cgaaatcgac     240
cctacgctta ccttcagacg aagttgtcgc gagggcattt gcggatcttg tgcgagaaaa     300
atcgacgggc agaacacgtt ggcctgtctc tgcaggattg ataggaatgc tgggaaggat     360
```

-continued

```
tcgaagatct atcccttacc acacagtgag tgtctcatct gagctctgcg tatctgagtg     420
ctaacttaga ttccagtgta catcgtcaag gacctcgtac cggatctcac ctacttctac     480
aagcagtaca agtctatcca accatacctt cagaacgaca acccacctgc gtcaggtctg     540
ttcattattt tgcaccctcc cctttgctcg gcttaccgaa tcgcttctag gtgaattcct     600
ccaaacgcaa gatgaccgca agaagctcga cggactctac gagtgtatcc tttgcgcgtg     660
ttgttcgacg tcttgccctt cgtattggtg gaaccaagac gaataccttg acccgctac      720 tttgatgcaa gcatatcgct ggatcgccga ctcgagagta cgttctgctc gtcgtatcat     780
gttttatctc atactgatat actcttagga ctcttatgcc gcagaacgca aggaaaagct     840
ccaaaacgag atgagcatgt accgatgcca cactatcttc aactgctcgc ggacatgccc     900
caagggtctc aaccccgctg ccgccatcgc gaaaatcaag cttgagcttg cggccgagta     960
a                                                                     961
```

<210> SEQ ID NO 4
<211> LENGTH: 267
<212> TYPE: PRT
<213> ORGANISM: Flammulina velutipes

<400> SEQUENCE: 4

```
Met Gln Ser Val Ala Arg Arg Phe Ser Ala Ala Val Arg Arg Ser
1               5                   10                  15

Phe Ser Thr Thr Ser Val Ala Phe Gln Ala Thr Pro Leu Glu Lys Pro
                20                  25                  30

Val Leu Asn Lys Glu Phe Lys Ile Tyr Arg Trp Asn Pro Asp Glu Pro
            35                  40                  45

Glu Lys Lys Pro Thr Leu Gln Ser Tyr Ile Ile Asp Leu Asn Gln Thr
        50                  55                  60

Gly Pro Met Ile Leu Asp Ala Leu Ile Lys Ile Lys Asn Glu Ile Asp
65                  70                  75                  80

Pro Thr Leu Thr Phe Arg Arg Ser Cys Arg Glu Gly Ile Cys Gly Ser
                85                  90                  95

Cys Ala Arg Lys Ile Asp Gly Gln Asn Thr Leu Ala Cys Leu Cys Arg
                100                 105                 110

Ile Asp Arg Asn Ala Gly Lys Asp Ser Lys Ile Tyr Pro Leu Pro His
            115                 120                 125

Met Tyr Ile Val Lys Asp Leu Val Pro Asp Leu Thr Tyr Phe Tyr Lys
        130                 135                 140

Gln Tyr Lys Ser Ile Gln Pro Tyr Leu Gln Asn Asp Asn Pro Pro Ala
145                 150                 155                 160

Ser Gly Glu Phe Leu Gln Thr Gln Asp Asp Arg Lys Lys Leu Asp Gly
                165                 170                 175

Leu Tyr Glu Cys Ile Leu Cys Ala Cys Cys Ser Thr Ser Cys Pro Ser
            180                 185                 190

Tyr Trp Trp Asn Gln Asp Glu Tyr Leu Gly Pro Ala Thr Leu Met Gln
        195                 200                 205

Ala Tyr Arg Trp Ile Ala Asp Ser Arg Asp Ser Tyr Ala Ala Glu Arg
    210                 215                 220

Lys Glu Lys Leu Gln Asn Glu Met Ser Met Tyr Arg Cys His Thr Ile
225                 230                 235                 240

Phe Asn Cys Ser Arg Thr Cys Pro Lys Gly Leu Asn Pro Ala Ala Ala
                245                 250                 255

Ile Ala Lys Ile Lys Leu Glu Leu Ala Ala Glu
            260                 265
```

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
ggcatttgcg gatcttgtgc gagaaa                                              26

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
acaacacgcg caaaggatac actcgta                                             27

<210> SEQ ID NO 7
<211> LENGTH: 34
<212> TYPE: DNA
<213> ORGANISM: Artificial Sequence
<220> FEATURE:
<223> OTHER INFORMATION: primer

<400> SEQUENCE: 7
gcgctgcagg catgcgagct cccaagcttg atcg                                     34

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
aattcgatca agcttgggag ctcgcatgcc tgcagcgc                                 38

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gcgctgcagg catgcgagct g                                                   21

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
cgggatccga tgcagtccgt cgcccgtc                                            28

<210> SEQ ID NO 11
<211> LENGTH: 28
<212> TYPE: DNA
<213> ORGANISM: Artificial Sequence -continued

```
<220> FEATURE:
<223> OTHER INFORMATION: primer

<400> SEQUENCE: 11
ggactagttt tgcttactcg gccgcaag                                          28

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
cgagatgagc atgtaccgat gcctcactat cttc                                   34

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
gaagatagtg aggcatcggt acatgctcat ctcgttttg                              39
```

CARBOXIN RESISTANCE GENE FOR *FLAMMULINA VELUTIPES*

FIELD OF THE INVENTION

The present invention pertains to a polynucleotide expressed in *Flammulina velutipes* against carboxin. In particular, the polynucleotide of the invention is a carboxin resistant gene specifically expressed in *Flammulina velutipes* against carboxin.

BACKGROUND OF THE INVENTION

Carboxin (IUPAC name: 5,6-dihydro-2-methyl-1,4-oxathiine-3-carboxanilide; CAS name: 5,6-dihydro-2-methyl-N-phenyl-1,4-oxathiin-3-carboxamide CAS; number: 5234-68-4) is a systemic agricultural fungicide and seed treatment agent. It is a respiratory toxin that prevents the oxidation of succinate by inhibiting the tricarboxylic acid cycle enzyme, succinate dehydrogenase (Sdh). This enzyme is composed of two subunits, a flavoprotein and an iron-sulphur protein (Ip), which together with two membrane-anchoring proteins make up succinate-quinone oxidoreductase. Carboxin is thought to act by preventing the transfer of electrons from succinate to ubiquinone through inhibiting the reoxidation of the high-potential S3 centre of the Ip subunit. Furthermore, Carboxin resistance in *Ustilago maydis* is known to be determined by a single amino acid residing in the Cys-rich cluster which ligates the S3 centre. A previous report indicated that insertion of the carboxin resistance (cbx R) gene into the *Ustilago maydis* genome impaired the pathogenic ability of the fungus towards *Zea mays*, the corn host, and that carboxin resistance did not significantly alter pathogenicity and was therefore a suitable marker for use in genetic analysis of *U. maydis* (Current Microbiology, Volume 44, Number, 2002, pp. 67-70).

Sensitivity (lack of resistance) to fungicides is a problem in commercial strains of mushrooms. Mutant strains, produced from known parent strains by UV irradiation followed by selection and having a genetically stable phenotype of insensitivity (resistance) to carboxin or benodanil, have now been prepared. The fungus *Verticillium fungicola* is pathogenic to mushrooms and is difficult to control. Certain fungicides, notably carboxin and benodanil, give some control over this pathogen, but these fungicides are phytotoxic to mushroom mycelium. If mushroom strains can be made less sensitive to one of these fungicides, fungicides can be used to control fungal diseases to which they are susceptible. U.S. Pat. No. 4,608,775 provided fungicide-resistant strains of the mushroom *Agaricus bisporus*. This prior reference selected an *Agaricus bisporus* strain against carboxin using UV irradiation but the gene resistant to carboxin was not identified. Toshikazu Irie et al. cloned genomic and cDNA fragments encoding the iron-sulfur protein (Ip) subunit of succinate dehydrogenase (EC 1.3.99.1) from the edible basidiomycetous fungus, *Pleurotus ostreatus* (Biochimica et Biophysica Acta 1396 (1998), 27-31). Furthermore, Toshikazu Irie et al. developed a selection marker gene for transformation of *Pleurotus ostreatus* by introducing a point mutation in a gene which encodes the iron-sulfur protein (Ip) subunit of succinate dehydrogenase (Curr Genet, 2000, 37: 209-212).

*Flammulina velutipes* (synonym: *Collybia velutipes*; common names: velvet foot; winter mushroom) is an edible agaric that is available in early spring or late fall when few other mushrooms are. It often occurs in clusters and has a viscid smooth orange to brown cap and a velvety stalk that turns black in maturity and pallid gills. *Flammulina velutipes* is a popular traditional foodstuff with high nutritive value and enhances immune function and resists cancer cells. However, no studies have been done on the carboxin resistance gene specifically expressed in *Flammulina velutipes* against carboxin. There is still a need to develop a selection marker gene against carboxin that is specifically expressed in *Flammulina velutipes*.

SUMMARY OF THE INVENTION

The present invention provides an isolated, carboxin resistant polynucleotide coding for a protein defined in (A) or (B): (A) a protein having the amino acid sequence of SEQ ID NO: 2, (B) a protein having the amino acid sequence of SEQ ID NO: 2 including substitution, deletion, insertion or addition of 1-20 amino acid residues and having carboxin resistant activity.

The present invention provides a carboxin resistant protein, which has the amino acid sequence of SEQ ID NO:2, and its variants having carboxin resistant activity.

The present invention also provides an expression vector comprising the polynucleotide of the invention.

The present invention also provides a host cell comprising the expression vector of the invention.

DETAILED DESCRIPTION OF THE INVENTION

Figure 1A:
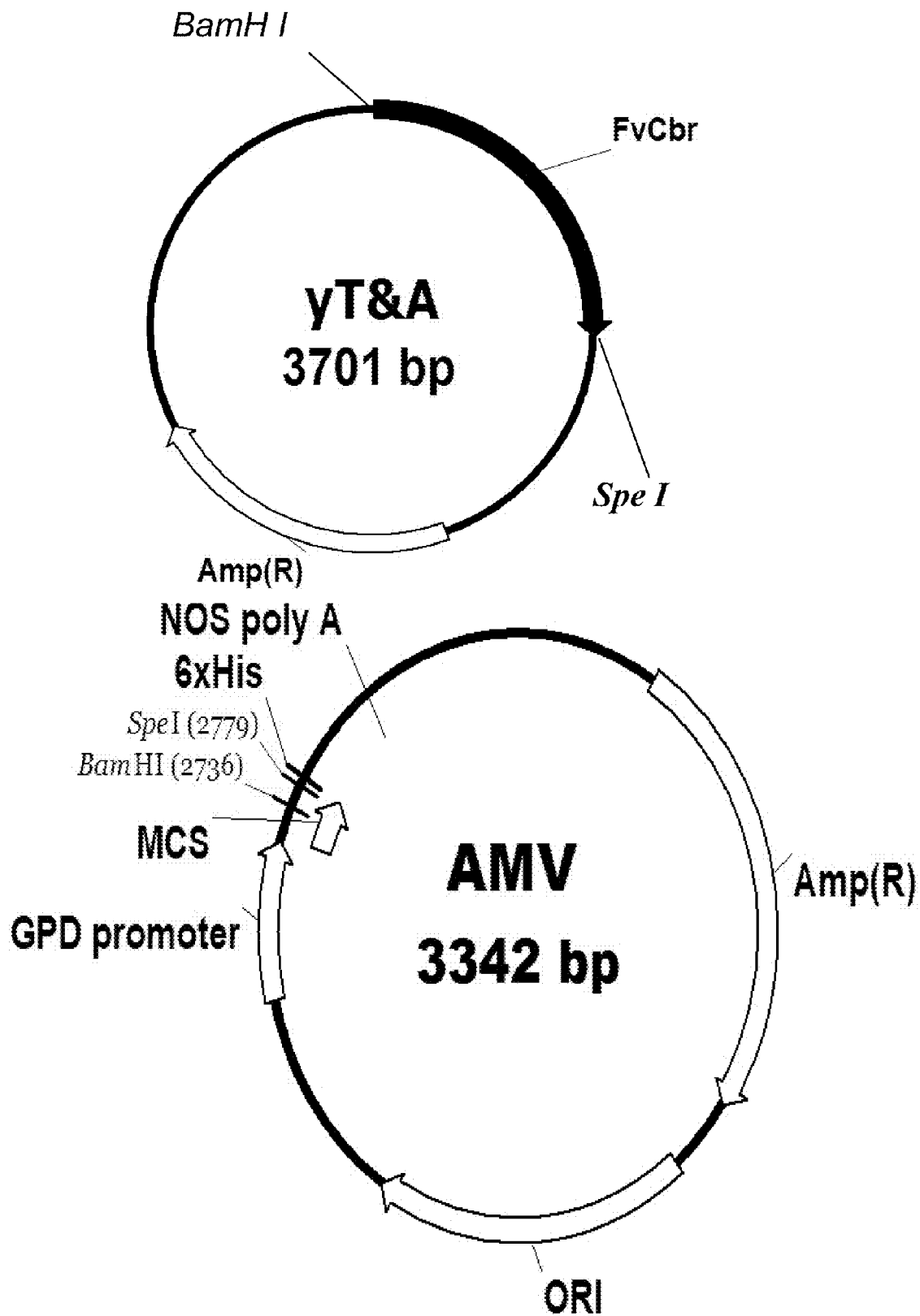
FIG. 1 shows FvCbrAMV vector (FIG. 1B) that is constructed by AMV vector (FIG. 1A) and yT&A vector (FIG. 1A) containing Cbr sequence.

The present invention developed a carboxin resistant gene specifically expressed in *Flammulina velutipes*. By expressing this carboxin resistant gene, *Flammulina velutipes* is able to resist carboxin.

DEFINITION

The term "isolated" means that the material is removed from its original environment, e.g., the natural environment if it is naturally occurring. For example, a naturally occurring polynucleotide or polypeptide present in a living organism is not isolated, but the same polynucleotide or polypeptide, separated from some or all of the coexisting materials in the natural system, is isolated. Such polynucleotides can be part of a vector and/or such polynucleotides or polypeptides can be part of a composition and still be isolated if such vector or composition is not part of its natural environment.

The term "gene" means all coding sequences between the start and stop codon of the carboxin resistant gene of the invention.

The term "carboxin resistant gene" or "carboxin resistant polynucleotide" refers to a polynucleotide sequence that encodes a polypeptide that exhibits carboxin resistant activity. As used herein, the term "carboxin resistant activity" refers to the ability of a substance, such as a polypeptide, to resist carboxin. A "carboxin resistant polypeptide" or "carboxin resistant protein" means a protein having carboxin resistant activity.

The term "polynucleotide" or "nucleotide" means polynucleotides comprising DNA. The polynucleotides of the embodiments also encompass all forms of sequences including, but not limited to, single-stranded forms, double-stranded forms, hairpins, stem-and-loop structures, and the like.

The terms "encoding" or "encoded" means that the polynucleotide or nucleic acid comprises the requisite information to direct translation of the nucleotide sequence into a specified protein. The information by which a protein is encoded is specified by the use of codons. A nucleic acid or polynucleotide encoding a protein may comprise non-translated sequences (e.g., introns) within translated regions of the nucleic acid or may lack such intervening non-translated sequences (e.g., as in cDNA).

The terms "polypeptide," "peptide," and "protein" are used interchangeably herein to refer to a polymer of amino acid residues. The terms apply to amino acid polymers in which one (or more) amino acid residue is an artificial chemical analogue of a corresponding naturally occurring amino acid, as well as to naturally occurring amino acid polymers.

The term "variants" means substantially similar sequences. For polynucleotides, a variant comprises a deletion and/or addition of one or more nucleotides at one or more internal sites within the polynucleotide of the invention and/or a substitution of one or more nucleotides at one or more sites in the polynucleotide of the invention. For polynucleotides, conservative variants include those sequences that, because of the degeneracy of the genetic code, encode the amino acid sequence of one of the carboxin resistant polypeptides of the embodiments. Variant polynucleotides also include synthetically derived polynucleotides encoding a carboxin resistant protein of the embodiments. Generally, variants of a particular polynucleotide of the embodiments will have at least about 50%, 55%, 60%, 65%, 70%, 75%, 80%, 85%, 90%, 91%, 92%, 93%, 94%, 95%, 96%, 97%, 98% and 99% or more sequence identity to that particular polynucleotide of the invention. "Variant" protein means a protein derived from the protein by deletion or addition of one or more amino acids at one or more internal sites in the protein and/or substitution of one or more amino acids at one or more sites in the protein of the invention. Variant proteins encompassed by the embodiments are biologically active, that is, they continue to possess the desired biological activity of the protein of the invention, namely, carboxin resistant activity as described herein. Biologically active variants of a carboxin resistant polypeptide of the embodiments will have at least about 50%, 55%, 60%, 65%, 70%, 75%, 80%, 85%, 90%, 91%, 92%, 93%, 94%, 95%, 96%, 97%, 98% and 99% or more sequence identity to the amino acid sequence for the protein of the invention as determined by sequence alignment programs and parameters described elsewhere herein. A biologically active variant of a protein of the embodiments may differ from that protein by as few as 1-20 amino acid residues, as few as 1-15 or 1-10, such as 6-10; as few as 5, or as few as 4, 3, 2, or even 1 amino acid residue.

The term "stringent conditions" refers to conditions where what is called a specific hybrid is formed but a non-specific hybrid is not formed. Under such conditions, for example, complementary strands of DNA consisting of a highly homologous nucleic acid, i.e., DNA consisting of a nucleotide sequence exhibiting about 65% or higher, preferably about 75% or higher, more preferably about 85% or higher, and most preferably about 95% or higher, homology to the nucleotide sequence as shown in SEQ ID NO: 1 hybridize, but complementary strands of a nucleic acid having homology lower than the aforementioned level do not hybridize. More specific conditions are constituted by a sodium concentration of 150 mM to 900 mM, preferably 600 mM to 900 mM, and a temperature of 60° C. to 68° C., and preferably 65° C.

The term "highly stringent" or "highly stringent condition" means conditions that permit hybridization of DNA strands whose sequences are highly complementary but exclude hybridization of significantly mismatched DNA. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides.

Nucleic acid hybridization methods are disclosed in detail by Kashima et al. (1985) Nature 313:402-404; Sambrook et al. (1989) Molecular Cloning: A Laboratory Manual, 2nd Ed., Cold Spring Harbor Laboratory, Cold Spring Harbor, N.Y. ("Sambrook") and Haymes et al., "Nucleic Acid Hybridization: A Practical Approach, IRL Press, Washington, D.C. (1985), all of which are incorporated herein by reference.

Carboxin Resistant Polynucleotide and Carboxin Resistant Protein of the Invention The present invention provides an isolated, carboxin resistant polynucleotide coding for a protein defined in (A) or (B): (A) a protein having the amino acid sequence of SEQ ID NO: 2, (B) a protein having the amino acid sequence of SEQ ID NO: 2 including substitution, deletion, insertion or addition of 1-20 amino acid residues and having carboxin resistant activity.

According to one embodiment of the invention, the isolated, carboxin resistant polynucleotide is hybridizable with a polynucleotide sequence complementary to the polynucleotide sequence having SEQ ID NO: 1 under a stringent condition, and which codes for a protein having carboxin resistant activity. Preferably, the hybridization is conducted under a highly stringent condition. According to a further embodiment of the invention, the isolated, carboxin resistant polynucleotide has a sequence as shown in SEQ ID NO: 1.

The present invention provides a carboxin resistant protein, which has the amino acid sequence of SEQ ID NO:2, and its variants having carboxin resistant activity. Preferably, the variants are the protein having the amino acid sequence of SEQ ID NO: 2 including substitution, deletion, insertion or addition of 1-20 amino acid residues and having carboxin resistant activity.

The invention cloned the gene encoding the iron-sulfur protein of succinate dehydrogenase from *Flammulina velutipes* that is called Carboxine gene (Cbr) of *Flammulina velutipes*. The sequence of this gene is shown as SEQ ID NO: 3 below:

```
                                              SEQ ID NO: 3
ATGCAGTCCGTCGCCCGTCGTTTCTCTGCCGCCGCCGTGCGCCGTAGCTTT

TCTACCACTTCTGTCGCGTTCCAGGCTACACCGCTCGAGAAGCCCGTGCTG

AACAAGGAATTCAAGATTTACCGCTGGAATCCTGATGAGCCGGAGAAGAAA

CCGACGCTACAGAGCTACATAATCGACCTGAACCAGACAGGGCCAATGATT

CTGGATGCTCTCATCAAGATTAAAAACGAAATCGACCCTACGCTTACCTTC

AGACGAAGTTGTCGCGAGGGCATTTGCGGATCTTGTGCGAGAAAAATCGAC
```

-continued
```
GGGCAGAACACGTTGGCCTGTCTCTGCAGGATTGATAGGAATGCTGGGAAG

GATTCGAAGATCTATCCCTTACCACACAGTGAGTGTCTCATCTGAGCTCTG

CGTATCTGAGTGCTAACTTAGATTCCAGTGTACATCGTCAAGGACCTCGTA

CCGGATCTCACCTACTTCTACAAGCAGTACAAGTCTATCCAACCATACCTT

CAGAACGACAACCCACCTGCGTCAGGTCTGTTCATTATTTTGCACCCTCCC

CTTTGCTCGGCTTACCGAATCGCTTCTAGGTGAATTCCTCCAAACGCAAGA

TGACCGCAAGAAGCTCGACGGACTCTACGAGTGTATCCTTTGCGCGTGTTG

TTCGACGTCTTGCCCTTCGTATTGGTGGAACCAAGACGAATACCTTGGACC

CGCTACTTTGATGCAAGCATATCGCTGGATCGCCGACTCGAGAGTACGTTC

TGCTCGTCGTATCATGTTTTATCTCATACTGATATACTCTTAGGACTCTTA

TGCCGCAGAACGCAAGGAAAAGCTCCAAAACGAGATGAGCATGTACCGATG

CCACACTATCTTCAACTGCTCGCGGACATGCCCCAAGGGTCTCAACCCCGC

TGCCGCCATCGCGAAAATCAAGCTTGAGCTTGCGGCCGAGTAA
```

The iron-sulfur protein of succinate dehydrogenase from *Flammulina velutipes* encoded by SEQ ID NO: 3 above (that is called "carboxin protein") has the amino acid sequence shown in SEQ ID NO: 4 below:

```
                                              SEQ ID NO: 4
MQSVARRFSAAAVRRSFSTTSVAFQATPLEKPVLNKEFKIYRWNPDEPEKK

PTLQSYIIDLNQTGPMILDALIKIKNEIDPTLTFRRSCREGICGSCARKID

GQNTLACLCRIDRNAGKDSKIYPLPHMYIVKDLVPDLTYFYKQYKSIQPYL

QNDNPPASGEFLQTQDDRKKLDGLYECILCACCSTSCPSYWWNQDEYLGPA

TLMQAYRWIADSRDSYAAERKEKLQNEMSMYRCHTIFNCSRTCPKGLNPAA

AIAKIKLELAAE
```

The invention has surprisingly found that a point mutation wherein His238 of SEQ ID NO:4 is altered and becomes Leu (CAC→CTC) results in carboxin resistance of the carboxin protein. The polynucleotide having the above point mutation is called "carboxin resistant polynucleotide" and the protein encoded by this polynucleotide is called "carboxin resistant protein." The sequences of the carboxin resistant polynucleotide and the carboxin resistant protein are respectively shown in SEQ ID NOs: 1 and 2 as follows:

```
                                              SEQ ID NO: 1
ATGCAGTCCGTCGCCCGTCGTTTCTCTGCCGCCGCCGTGCGCCGTAGCTTT

TCTACCACTTCTGTCGCGTTCCAGGCTACACCGCTCGAGAAGCCCGTGCTG

AACAAGGAATTCAAGATTTACCGCTGGAATCCTGATGAGCCGGAGAAGAAA

CCGACGCTACAGAGCTACATAATCGACCTGAACCAGACAGGGCCAATGATT

CTGGATGCTCTCATCAAGATTAAAAACGAAATCGACCCTACGCTTACCTTC

AGACGAAGTTGTCGCGAGGGCATTTGCGGATCTTGTGCGAGAAAATCGAC

GGGCAGAACACGTTGGCCTGTCTCTGCAGGATTGATAGGAATGCTGGGAAG

GATTCGAAGATCTATCCCTTACCACACAGTGAGTGTCTCATCTGAGCTCTG

CGTATCTGAGTGCTAACTTAGATTCCAGTGTACATCGTCAAGGACCTCGTA

CCGGATCTCACCTACTTCTACAAGCAGTACAAGTCTATCCAACCATACCTT

CAGAACGACAACCCACCTGCGTCAGGTCTGTTCATTATTTTGCACCCTCCC

CTTTGCTCGGCTTACCGAATCGCTTCTAGGTGAATTCCTCCAAACGCAAGA

TGACCGCAAGAAGCTCGACGGACTCTACGAGTGTATCCTTTGCGCGTGTTG

TTCGACGTCTTGCCCTTCGTATTGGTGGAACCAAGACGAATACCTTGGACC

CGCTACTTTGATGCAAGCATATCGCTGGATCGCCGACTCGAGAGTACGTTC

TGCTCGTCGTATCATGTTTTATCTCATACTGATATACTCTTAGGACTCTTA

TGCCGCAGAACGCAAGGAAAAGCTCCAAAACGAGATGAGCATGTACCGATG

CCTCACTATCTTCAACTGCTCGCGGACATGCCCCAAGGGTCTCAACCCCGC

TGCCGCCATCGCGAAAATCAAGCTTGAGCTTGCGGCCGAGTAA
```

```
                                              SEQ ID NO: 2
MQSVARRFSAAAVRRSFSTTSVAFQATPLEKPVLNKEFKIYRWNPDEPEKK

PTLQSYIIDLNQTGPMILDALIKIKNEIDPTLTFRRSCREGICGSCARKID

GQNTLACLCRIDRNAGKDSKIYPLPHMYIVKDLVPDLTYFYKQYKSIQPYL

QNDNPPASGEFLQTQDDRKKLDGLYECILCACCSTSCPSYWWNQDEYLGPA

TLMQAYRWIADSRDSYAAERKEKLQNEMSMYRCLTIFNCSRTCPKGLNPAA

AIAKIKLELAAE
```

According to the invention, the point mutation can be conducted by any method known in the art. For example, the point mutation may be conducted by using mutagens such as radiation from UV rays, X-rays or extreme heat, chemicals (molecules that misplace base pairs or disrupt the helical shape of DNA), site-directed mutagenesis or a commercial point mutation kit. According to one preferred embodiment of the invention, the site-directed mutagenesis or point mutation kit is an option when conducting the point mutation.

Accordingly, the isolated, carboxin resistant polynucleotide of the invention includes the polynucleotides coding for a protein defined in (A) or (B): (A) a protein having the amino acid sequence of SEQ ID NO: 2, (B) a protein having the amino acid sequence of SEQ ID NO: 2 including substitution, deletion, insertion or addition of 1-20 amino acid residues and having carboxin resistant activity.

The present invention also provides an expression vector comprising the polynucleotide of the invention. Furthermore, the present invention provides a host cell comprising the expression vector of the invention.

The expression vector, according to this invention, comprises the selected DNA of the DNA sequences of this invention for expression in a suitable host. The DNA is operatively joined in the vector to an expression control sequence in the recombinant DNA molecule so that normal or mutant protein can be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cells to be transfected with the vectors of this invention may be from a host selected from the group consisting of yeasts, fungi, insects, mice or other animals or plant hosts or may be human tissue cells. For the mutant DNA sequence, similar systems are employed to express and produce the mutant protein.

The carboxin resistant gene of the invention gives *Flammulina velutipes* resistance against carboxin. Furthermore, the mutated carboxin resistant gene of *Flammulina velutipes* would provide a potentially valuable selectable marker for the development of transformation vectors.

EXAMPLE

Example 1

Cloning of Full Length Carboxine (Cbr) Gene Sequence of *Flammulina velutipes*

Extraction of DNA

The mycelia of *Flammulina velutipes* were cultured with 50 ml protein liquid medium containing malt extract at 25° C. for three weeks. The resulting mycelia were washed with sterile water and then lyophilized to remove water. The mycelia were ground into powder under liquid nitrogen. 50 mg dried mycelia powder were added to 600 µl lysis buffer and then 600 µl PCI (phenol:chloroform:Isoamylalcohol=25:24:1) were added to remove protein and impurities. The water layer was taken out and 3M sodium acetate and isopropanol were added so that DNA was precipitated. The DNA precipitates were washed with 70% ice alcohol several times. After the alcohol was volatilized, 100 µl TE buffer and RNase were added to the DNA precipitates at 37° C. After 1 hour of reaction, 100 µl chloroform were added and the water layer was taken. 3M sodium acetate and isopropanol were added to the resulting water layer to precipitate DNA again. The precipitated DNA was dissolved in 100 µl sterile water and stored at a temperature below −20° C.

Cloning of Cbr of *Flammulina velutipes*

The degenerate primers Cbr2F (5′-ggCATTTgCggATCT-TgTgCgAgAAA; SEQ ID NO:5) and Cbr2R (5′-ACAA-CACgCgCAAAggATACACTCgTA; SEQ ID NO:6) were used to perform the degenerate PCR and the PCR reaction conditions were as follows:

Initial denature temperature and time:95° C., 2 minutes

Denature temperature and time:95° C., 1 minute
Anneal temperature and time:40° C., 30 seconds } 35 cycles
Extension temperature and time:72° C., 1.5 minutes Initial denature temperature and time: 95° C., 2 minutes
Denature temperature and time: 95° C., 1 minute
Anneal temperature and time: 40° C., 30 seconds 35 cycles
Extension temperature and time: 72° C., 1.5 minutes
Final extension temperature: 72° C., 10 minutes The amplified PCR products were analyzed by electrophoresis on agarose gel. The 400 by band was taken and purified with Qiagen PCR purification kit. The resulting DNA was preserved in yT&A vector by TA cloning and then transformed into *E. coli* DH5α. The resulting DNA was sequenced to identify the partial sequence of Cbr.

Comparison of Sequence and Cloning of Amplified Sequence

The resulting gene sequence was compared and analyzed by BioEdit software v 7.0.0 (Ibis Therapeutics Carlsbad, Calif.). To identify the full length of Cbr sequence, the genome walking method was used (Nucleic Acids Research, 2000, Vol. 28, No. 11, e55). The chromosomal DNA was sliced by the above-mentioned seven restriction enzymes and then the adaptors with the same restriction sites were ligated. In accordance with the partial Cbr sequence, gene specific primers were designed and they in combination with MKP24 primer complementary to the adaptor sequence were used to target unknown fragment sequences by PCR. Seven restriction enzymes, BamHI, EcoRI, HindIII, KpnI, PvuII, PstI and XbaI, were used in the preparation of template DNA. The adaptor primers MKP22 (5′-GCGCTGCAGGCATGC-GAGCTCCCAAGCTTGATCG; SEQ ID NO:7), MKP23 (5′-AATTCGATCAAGCTTGGGAGCTCGCAT-GCCTGCAGCGC; SEQ ID NO:8) and MKP24 (5′-GCGCT-GCAGGCATGCGAGCTG; SEQ ID NO:9) were used in the template preparation. Annealing of the two primers MKP22 and MKP23 to form the double-stranded oligo-cassette MKD1 was performed by boiling a 100 mM solution of the primers, followed by slow cooling to room temperature. Primers were supplied by GATCopenhagen Aps (Symbion, Copenhagen, Denmark). For the construction of the oligo-cassette library, EcoRI digested chromosomal DNA was ligated to MKD1 oligo-cassette at a 10-fold molar excess of the cassette, and then column purification of the ligation products was conducted, where unbound cassette DNA was removed (GFXTM PCR DNA and gel band purification kit, Amersham Pharmacia Biotech, Hørsholm, Denmark). An oligo-cassette-specific primer MKP24, which spans the SacI-PstI region on MKD1, was synthesised for amplification of DNA ligated to the oligo-cassette. Upon digestion of MKD1 with HindIII and de-phosphorylation using calf intestinal phosphatase, the HindIII-specific oligo-cassette MKD3 was constructed. The genome walking was performed in the direction of 5′ to 3′ to target the full length of Cbr sequence.

Analysis of Cbr Sequence of *Flammulina velutipes*

The alignment and analysis of the resulting Cbr sequence was performed by BioEdit version 7.0.2 and the similarity between the Cbr sequence and its protein was determined by using NCBI database. The Cbr sequence is as shown in SEQ ID NO: 3.

Example 2

Point Mutation of Cbr Sequence of *Flammulina velutipes*

The vector used to express Cbr sequence was AMV vector, which has GPD promoter of *Agaricus bisporus* and was developed by the applicant. The full length of Cbr sequence was amplified by using CbrFv9FB (5′-cgggatccGATG-CAGTCCGTCGCCCGTC; SEQ ID NO:10)/CbrFv10Rs (5′-ggactagtTTTGCTTACTCGGCCGCAAG; SEQ ID NO:11) primer pair so that the Cbr sequence had BamH I and Spe I restriction sites. The resulting sequence was sequenced and confirmed by TA cloning.

Figure 1B:
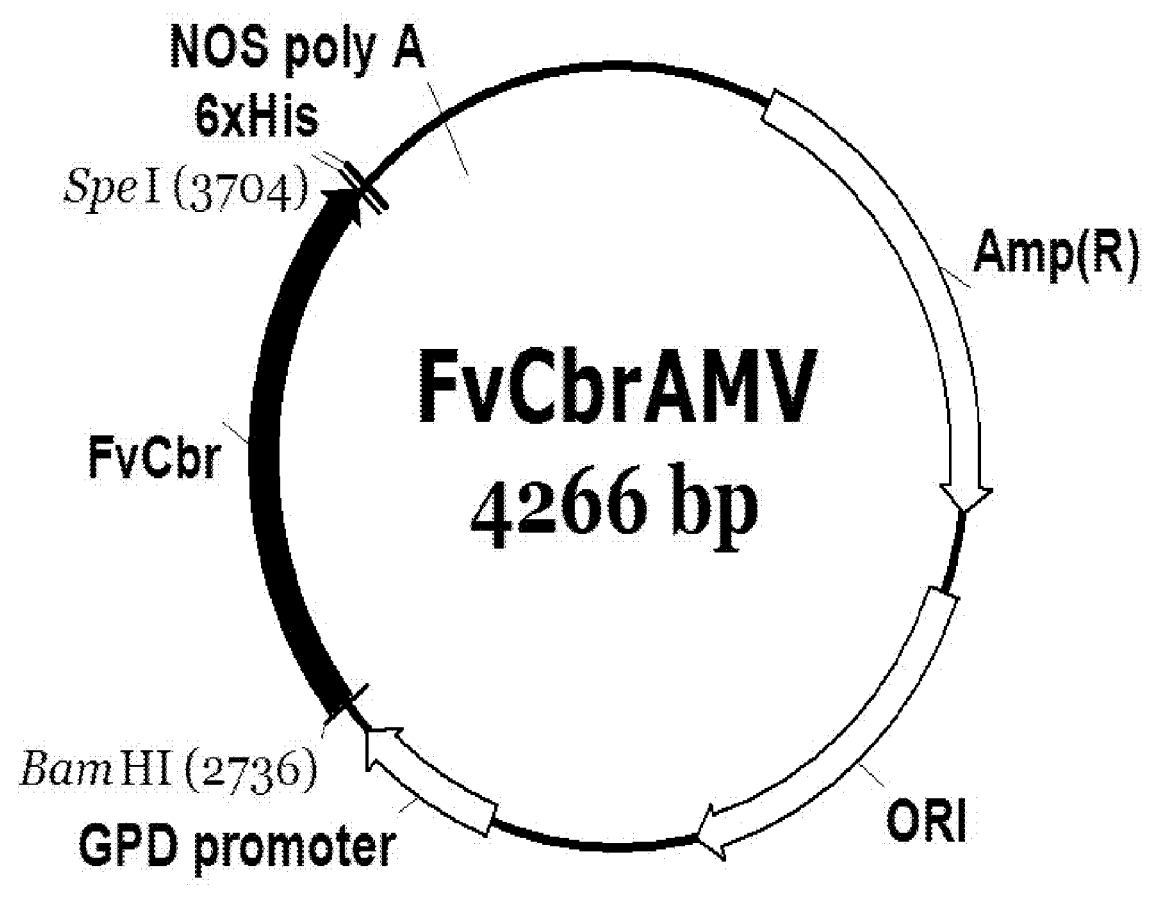

The full length Cbr sequence preserved in yT&A vector (FIG. 1A) was sliced by BamH I and Spe Ito obtain FvCbr. After the AMV (FIG. 1A) vector was also sliced by BamH I and Spe I, the Cbr sequence was ligated to the corresponding sites in AMV vector. The vector including Cbr sequence and GPD promoter was called "FvCbrAMV" (FIG. 1B).

A point mutation of the Cbr sequence was conducted using CbrFv11FD (5′-cgagatgagcatgtaccgatgccTcactatcnc; SEQ ID NO:12)/CbrFv14Rd (5'-gaagatagtgAggcatcggtacatgct-catctcgattg; SEQ ID NO:13) primer pair and QuikChange® Site-Directed Mutagenesis Kit. The mutated sequence was sequenced to confirm the point mutation and the vector harboring the mutant Cbr sequence (AMV+mCbr) was called "mFvCbrAMV."

The mutated sequence above is shown in SEQ ID NO:1.

Example 3

Test for the Function of Cbr Sequence

Figure 2A:
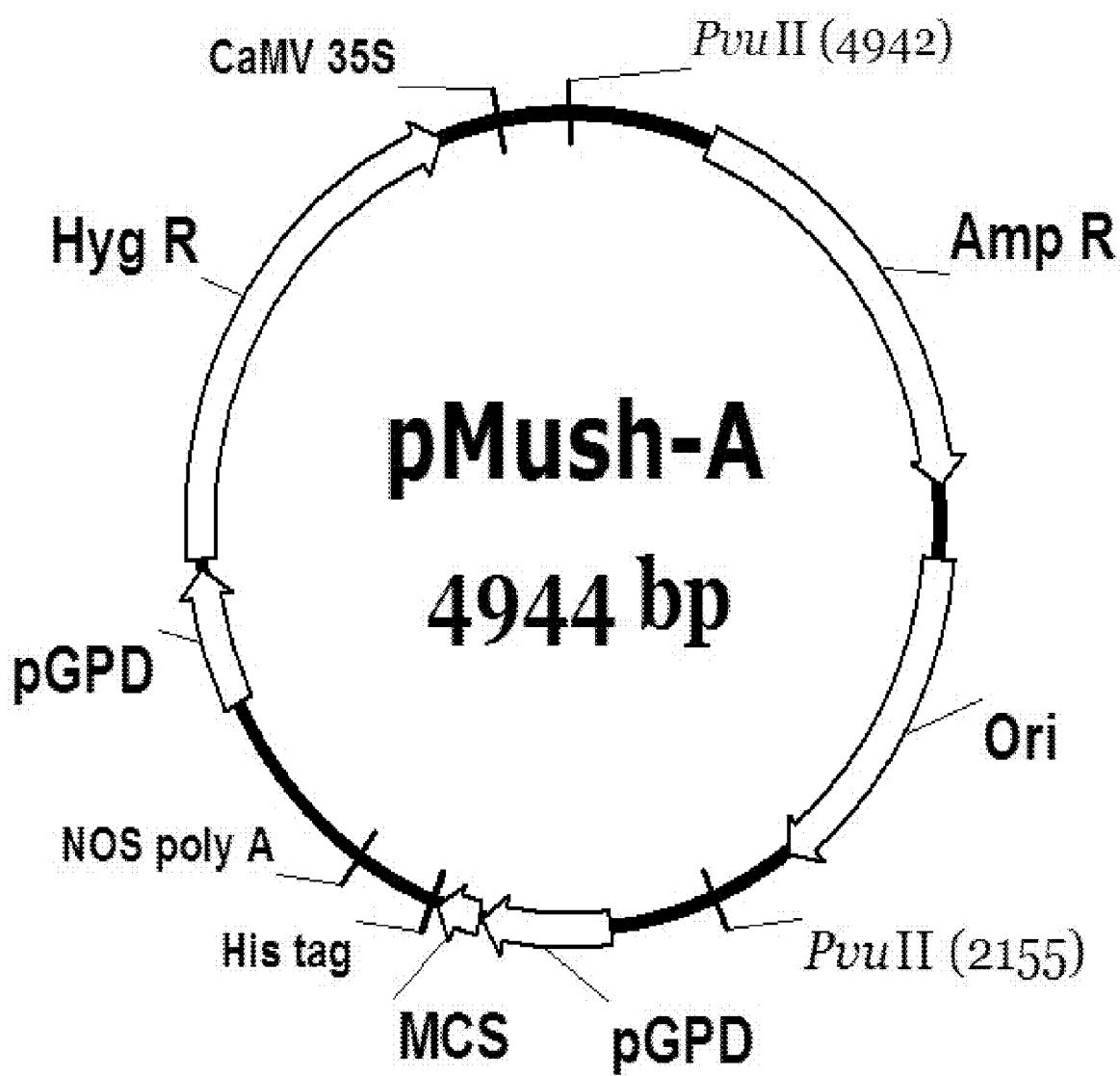
FIG. 2 shows pMush-A-mFvCbr (FIG. 2B) that is constructed by mFvCbrAMV vector (FIG. 2A) and pMush-A vector (FIG. 2A) that contains the GPD promoter (pGPD).
Figure 2B:
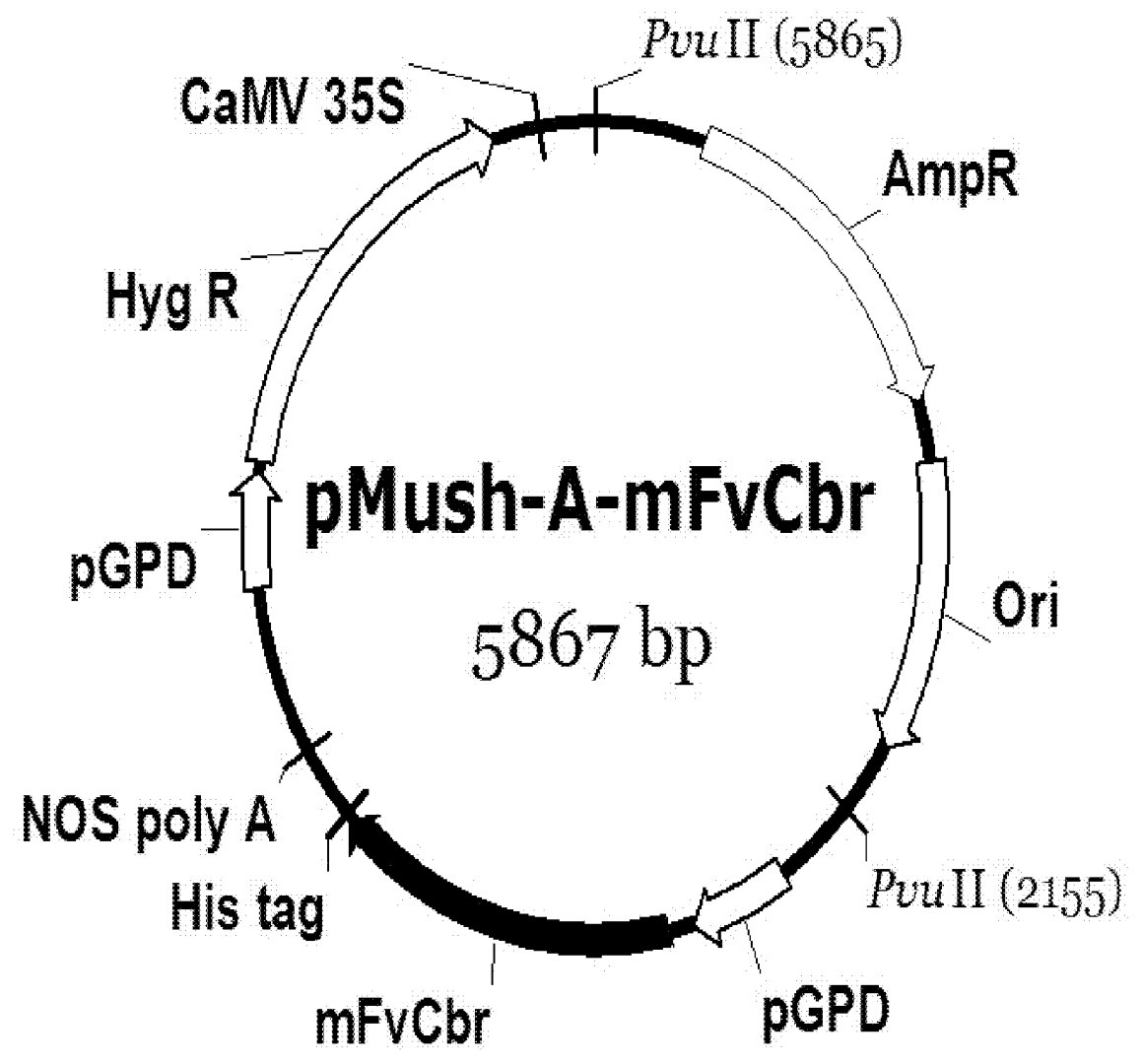

The vector for expressing mutant Cbr sequence is pMush-A vector containing GPD promoter (pGPD) and hygromycin resistance (hyg) marker. This pMush-A vector is shown in FIG. 2A. The mutant Cbr sequence preserved in mFvCbrAMV vector (FIG. 1B) and pMush-A vector were sliced with BamH I and Spe I, respectively. The mutant Cbr sequence (mFvCbr) was ligated to the corresponding sites in pMush-A vector using T4 DNA ligase. The constructed vector is called pMush-A-mFvCbr (FIG. 2B).

Figure 3:
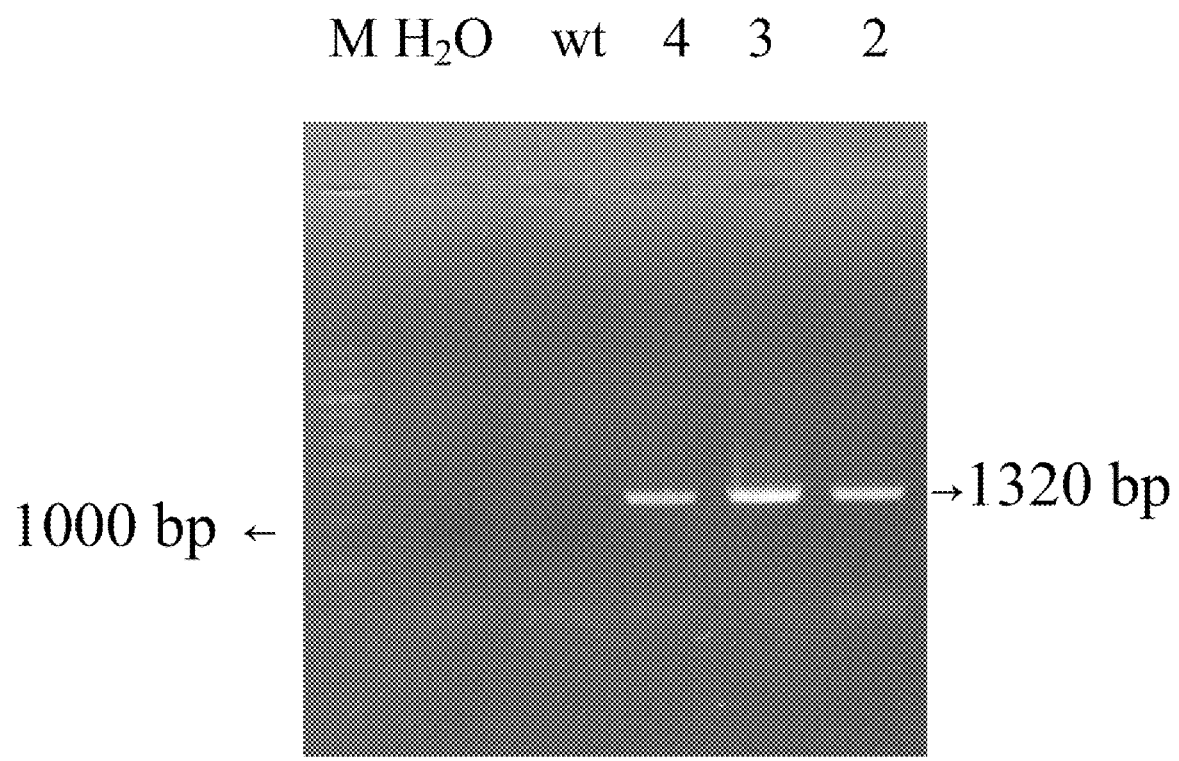
FIG. 3 shows the electrophoresis plot for the hygromycin gene of the wild-type *Flammulina velutipes* and the *Flammulina velutipes* transformants, wherein bands 2, 3 and 4 are *Flammulina velutipes* transformants, wt is the wild-type *Flammulina velutipes*, H$_2$O is a negative control and M is a marker.

The mycelia of *Flammulina velutipes* were cultured in PDB medium at 25° C. for 1-2 weeks. The resulting mycelia were disrupted by a homogenizer and then treated with lysing enzyme solution containing lysing enzyme (Sigma, St. Louis, Mo., U.S.A.), mannitol and potassium phosphate buffer. The resulting mycelial fragments were dissolved in 100 μl electroporation buffer solution as the competent cells used in the electroporation. The well-prepared competent cells were added to the mutant Cbr DNA solution obtained from Example 2 and then placed on ice for 10 minutes. An electroporation was conducted for the resulting solution using Electro Cell Manipulator ECM 630 Electroporation System (BTX, San Diego, Calif., U.S.A.) to obtain transformed mycelia. The resulting mycelial solution was plated on PDA plate medium containing 2 μg/ml Carboxin and 0.6 M mannitol and at 25° C. for selection. Ten transformed strains were selected and cultured in PDA plate medium containing 2 mg/ml carboxin for one week. Four strains grew in the PDA plate medium, indicating that these strains have the mutant Cbr DNA of the invention. The growth of these strains proves that the mutant Cbr DNA of the invention was successfully transformed and expressed. The genomic DNA of the strains was extracted and amplified using Hyg primer. The wild-type *Flammulina velutipes* which lacks the Hyg marker was used as the negative control. As shown in the electrophoresis plot of FIG. 3, a 1320 by fragment appeared, so the transformed strains contained Anti-Hyg sequence. This result proves that the strains contained the p-MUSH-A-mFvCbr sequence and were transformed with the Cbr mutant of the invention successfully.

What is claimed is:

1. An isolated, polynucleotide coding for a protein having the amino acid sequence of SEQ ID NO: 2.

2. The isolated polynucleotide according to claim 1, which has the sequence of SEQ ID NO:1.

3. An expression vector comprising the polynucleotide of claim 1.

4. A host cell comprising the expression vector of claim 3.

* * * * *